United States Patent [19]

Reiss

[11] 4,185,619

[45] Jan. 29, 1980

[54] RETRACTABLE SHIELD FOR SYRINGES

[75] Inventor: James M. Reiss, Center Moriches, N.Y.

[73] Assignee: Atomic Products Corporation, Center Moriches, N.Y.

[21] Appl. No.: 636,811

[22] Filed: Dec. 1, 1975

[51] Int. Cl.² .............................................. A61N 5/12
[52] U.S. Cl. ...................................... 128/1.1; 128/215
[58] Field of Search ............ 128/1.1, 2 A, 215, 218 R, 128/218 P, 218 F; 250/506, 515, 512, 513; 285/317, 298, DIG. 12

[56] References Cited

U.S. PATENT DOCUMENTS

| 167,675 | 9/1875 | Koehler | 285/317 |
|---|---|---|---|
| 3,596,659 | 8/1971 | Glasser | 128/215 |
| 3,655,985 | 4/1972 | Brown et al. | 250/506 X |
| 3,673,411 | 6/1972 | Glasser | 250/506 |
| 3,769,490 | 10/1973 | Czaplinski | 250/506 X |
| 3,814,941 | 6/1974 | Czaplinski | 128/1.1 X |
| 3,820,541 | 6/1974 | Langan | 128/1.1 X |
| 3,863,623 | 2/1975 | Trueblood et al. | 128/2 A |
| 3,973,554 | 8/1976 | Tipton | 128/1.1 |

Primary Examiner—John D. Yasko
Attorney, Agent, or Firm—Charles E. Temko

[57] ABSTRACT

An improved shield for enclosing the body of a hypodermic syringe to protect a user against exposure from radioactive materials. The shield is formed of two elements, including an upper element having means for engaging the barrel of the syringe, and preferably formed from lightweight metallic materials such as aluminum. A second element formed of tantalum, tungsten, depleted uranium alloy or other dense material offering a high degree of radioactivity shielding is slideably disposed within the first element, and adapted to be retracted in telescopic fashion for dose calibration and subsequent return to an adjustable extended position to cover the lower end of the syringe barrel in which the radioactive contents are contained. Without modification, this syringe shield provides for the accommodation of syringes of different manufacture having different barrel diameters, effective lengths, graduation orientation and flange geometry. A novel clamp disposed at the upper end of the upper element accommodates for differing syringe diameters. Lockable clamping means on a lower element fixing the relative position between the upper and lower elements accommodates for the differing effective syringe barrel lengths.

2 Claims, 8 Drawing Figures

U.S. Patent    Jan. 29, 1980    4,185,619
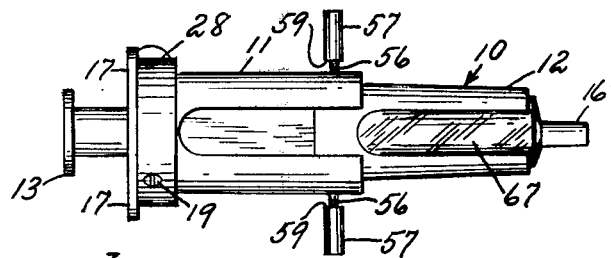
FIG. 1
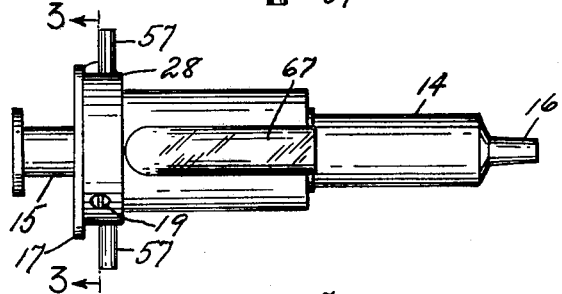
FIG. 2
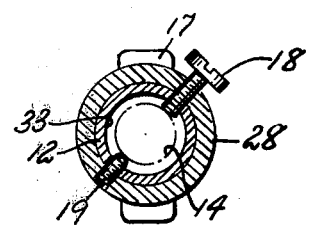
FIG. 3
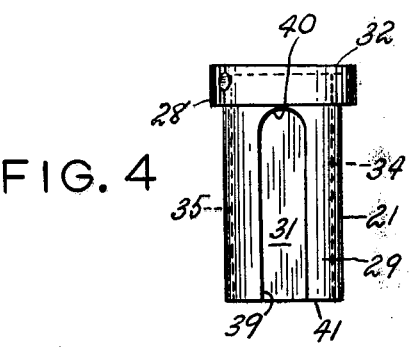
FIG. 4
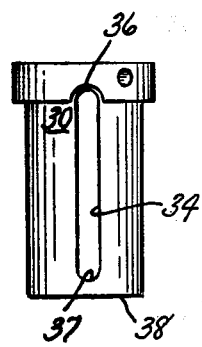
FIG. 5
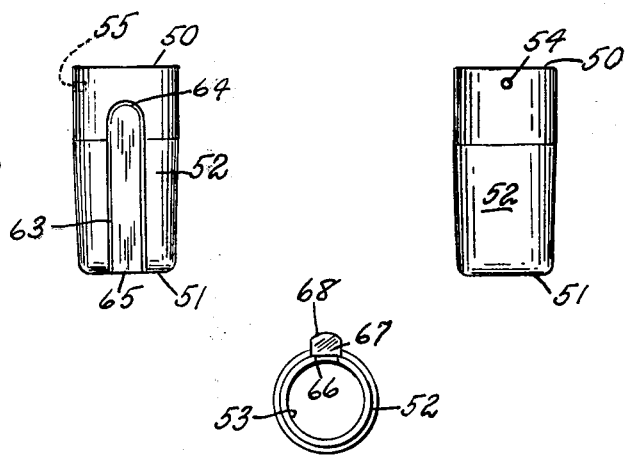
FIG. 6
FIG. 7
FIG. 8

RETRACTABLE SHIELD FOR SYRINGES

BACKGROUND OF THE INVENTION

It is well known in the art to provide removable shielding adapted to engage a hypodermic syringe in such manner as to surround the barrel thereof and thereby shield a user from radiation emanating from the radioactive contents of the syringe. Most such devices include a bayonet-type locking means at the upper end thereof adapted to engage the outwardly projecting syringe flanges formed integrally with the barrel and normally contacted by the fingers of the user during the discharge of the syringe. Prior art syringe shields also include a single shield barrel formed of lead which covers the major portion of the length of the syringe barrel, leaving an exposed lower syringe end to permit determination of whether or not the syringe is loaded.

There are several disadvantages in the use of this construction. One is the substantial weight of the lead shielding, often heavier than the weight of the syringe itself, and tending to make manipulation of the syringe awkward. Another is the fact that the exposed lower end of the syringe is the point of greatest radiation, and it is normally exposed at all times. Further, in order to calibrate the radiopharmaceutical dose in the syringe, it is usually necessary to remove the syringe from engagement within the shield, and during this process, the user is fully exposed to radiation. While such radiation is normally not dangerous to a patient, it is to be appreciated that the technician using the syringe is exposed to similar radiation on a daily basis, the total accumulation of such radiation being inherently dangerous. The term dose calibration is intended to mean, in this specification, the placing of a loaded syringe in the proximity of radiation measuring means, rather than the loading of the syringe to a predetermined volume. This dose calibration is preferably accomplished immediately before use, since the radioactive materials normally injected decay very rapidly, and often lose all effective strength over the course of several days.

There has recently been developed by the National Institutes of Health, Bethesda, Md., an improved shield made in two parts, including an upper shield element arranged in telescopic fashion with respect to a lower shield element, the upper shield element being of lightweight metal, the lower being of very dense metal such as tantalum or tungsten. This structure permits the confining of shielding material in the area where radiation is greatest, namely at the lower end of the barrel, and the retraction of the lower shield for dose calibration without the necessity of completely removing the shield from the syringe. As might be expected, the cost of manufacture of such devices results in a very high unit cost, making desirable the ability to use the shield with syringes of different manufacture, having different barrel lengths, graduation orientation, diameters, and flange geometry which may vary substantially in comparable syringes of the same capacity. It is further desirable that means be provided for maintaining the sliding relation between the upper and lower shield elements in fixed adjustment to accommodate the aforementioned corresponding differences in syringe construction.

SUMMARY OF THE INVENTION

Briefly stated, the invention contemplates the provision of an improved syringe shield of the class described, including first and second generally tubular elements arranged in mutually telescopic relation. The upper element is formed of lightweight material, such as aluminum, and includes an adjustable means for engaging the barrel of a syringe, such that irrespective of syring barrel diameter, length, graduation orientation and flange geometry, the axis of the barrel may be adjusted to be coaxial with respect to the longitudinal axis of the upper shield element. The lower shield element is formed of tantalum, depleted uranium or tungsten, materials which are at least 50% denser than lead, and possessed of the structural strength of steel. To reduce bulk and weight, the essential high density shielding is confined only to that part of the syringe volume actually loaded with a radionuclide. The end of the shield is tapered to allow the user maximum mobility and berth while making the venipuncture. The lower element is provided with a side opening supporting an elongated piece of lead glass which allows visibility of the graduations on the barrel of the syringe. The upper element includes slotted openings engaging threaded projections carried by the lower element, the threaded projections carrying set screw means which are manually adjustable such that the lower element may be positively locked either in retracted position, or an extended position corresponding to the effective length of the barrel of the particular syringe being used.

BRIEF DESCRIPTION OF THE DRAWING

In the drawing, to which reference will be made in the specification, similar reference characters have been employed to designate corresponding parts throughout the several views.

FIG. 1 is a side elevational view of an embodiment of the invention, showing the same in fully extended condition upon a conventional hypodermic syringe.

FIG. 2 is a similar elevational view of the embodiment, with a lower element thereof in retracted position.

FIG. 3 is a transverse sectional view as seen from the plane 3—3 in FIG. 2.

FIG. 4 is a side elevational view of an upper element comprising a part of the embodiment.

FIG. 5 is a side elevational view of the upper element, as seen from the right hand portion of FIG. 4.

FIG. 6 is a side elevational view of a lower element comprising a part of the embodiment.

FIG. 7 is a side elevational view of the lower element as seen from the right hand portion of FIG. 6.

FIG. 8 is a bottom plan view of the lower element.

DETAILED DESCRIPTION OF THE DISCLOSED EMBODIMENT

In accordance with the invention, the device, generally indicated by reference character 10, comprises broadly: a first or upper shield element 11 and a second or lower shield element 12. In FIGS. 1 and 2 in the drawing, the device 10 is shown in engaged condition upon a conventional syringe 13, including a barrel element 14, a plunger element 15, a detachable needle supporting member 16 and a pair of finger engaging flanges 17, normally molded integrally with the barrel element 14. The details of the syringe 13 are well known in the art, and form no part of the present disclosure.

The upper element 11 is preferably formed of lightweight material, such as aluminum and alloys thereof. It includes a first syringe barrel engaging clamp member 18 in the form of a threaded screw, and a resilient ball detent screw 19 coaxially alined with the axis of the member 18, the pair forming clamping means engaging the barrel of the syringe. By adjusting the setting of the screw against the ball detent, after aligning the syringe graduations directly behind a lead glass window in the shield, it is possible to center the axis of the barrel of the syringe relative to the principal longitudinal axis of the upper shield element 11.

The barrel 21 of the shield element 11 includes an integral upper collar 28 in which the members 18 and 19 are disposed, and a sleeve 29. The latter is bounded by an outer surface 30, an inner surface 31, and an upper peripheral surface 32 determining one end of a bore 33. A pair of radially oppositely disposed slotted openings 34 and 35 include upper closed ends 36 and lower closed ends 37, the latter being disposed immediately above a lower peripheral edge 38. Located at 90° with respect to each of the slotted openings 34 and 35 is a wider slot 39 having a closed upper end 40 and an open lower end 41.

The lower shield element 12 as has been mentioned, is formed from a material providing an effective radoactivity shield. The element 12 is also of cylindrical configuration, bounded by an upper edge surface 50, a lower end surface 51, an outer surface 52 and an inner surface 53. Bordering the upper edge surface 50 are first and second tapped openings 54 and 55, respectively, each engaging a threaded shaft 56, in turn threadedly engaging a head member 57 urged inwardly by manual rotation to a point where the inner surfaces 59 will bear upon the outer surface of the first element in areas adjacent the slotted openings 34 and 35 to lock the position of the lower element 12 relative to the upper element 11. Adjustment, once a syringe has been installed need normally only be made at the time of dose calibration, and when extended, the position of the lower element is locked. It may remain so during injection of the contents of the syringe into the vein of a patient.

An open-ended slot 63 is coaxially alined with the wider slot 39 in the first element 11, and extends from an upper end 64 to a lower end 65. A shoulder 66 (FIG. 8) is provided to support an elongated lead glass insert 67, the upper surface 68 of which may be curved to provide a degree of magnification for the viewing of the graduations on the barrel of the syringe.

During the loading of the syringe, if dose calibration will be made immediately thereafter, the lower element may be retracted to a point where the lower edge thereof overlies the graduation at which the loading operation is complete. Thus, the lower edge of the lower element may be used as a guide. Alternatively, the lower element may be left in extended condition, and the graduations viewed through the lead glass insert 67. As soon as loading has been accomplished, and dose calibration completed, the lower element is returned to the extended condition corresponding to the length of the syringe barrel, wherein it may completely shield the inducted radioactive contents. The loaded condition of the syringe may be observed, at any time prior to use, without disturbing the shield which offers complete protection, and the venipuncture may be made prior to the emptying of the contents of the syringe without retraction of the shield. This ability is enhanced by the fact that the lower element is slightly tapered in a downward direction.

It may thus be seen that I have invented novel and highly useful improvements in syringe shields, in which maximum radiation protection to the user is afforded by virtue of the fact that the shield, under normal circumstances, need not be detached from the syringe at any time. The syringe shield is formed to include two elements, only a lower of which is formed of high density radioactivity shielding material, thus effectively reducing the total weight of the device, this expedient taking advantage of the fact that most syringes used in the injection of radioactive materials are seldom filled to more than one half of total capacity. Although the cost of materials from which the lower element is made is not inconsiderable, the structural strength of the same is far superior to lead, and by virtue of my novel syringe engaging means, not only may syringe barrels of different outer diameters, graduation orientation and flange geometry be accommodated in coaxial relation with respect to the shield elements, but the ability of the lower shield to shift relative to the upper shield element enables the accommodation of syringe barrels of different effective lengths as well. The use of lightweight aluminum alloy for the upper element and depleted uranium of optimal shielding property in the lower element permits maximum taper at the needle end of lower element allowing closer positioning of my device to patient's vein for venipuncture. This combination of materials makes it possible to obtain maximum shielding effect at minimum overall weight for easy maneuverability during use.

I wish it to be understood that I do not consider the invention limited to the precise details of structure shown and set forth in this specification, for obvious modifications will occur to those skilled in the art to which the invention pertains.

I claim:

1. In an improved shield for enclosing a hypodermic syringe containing radioactive materials, including a first shield element of generally hollow cylindrical configuration defining an axially oriented bore, and a second shield element of hollow cylindrical configuration having an outer diameter corresponding to the inner diameter of said bore in said first shield element, improved means for selectively accommodating a plurality of syringes having barrel elements of differing overall diameter, effective length, reticle orientation and flange design, in shielded relation, said means including: a radially extending threaded bore on an upper end of said first shield element, a threaded screw engaged within said threaded bore and penetrating said axially oriented bore; a resilient member having a line of action coaxially positioned relative to the axis of said screw, said resilient means and screw selectively contacting the outer surface of an engaged syringe barrel, adjustment of said screw serving to center the axis of said syringe barrel relative to the axis of said axially oriented bore in said first shield element.

2. Structure in accordance with claim 1, further characterized in the provision of said screw means on said second shield element penetrating slotted openings in said first shield element for locking the position of the former relative to the latter, whereby to position the lower end of said second shield element in overlying position relative to the lower end of an engaged syringe barrel.

* * * * *